(12) United States Patent
Seyfang et al.

(10) Patent No.: US 11,788,155 B1
(45) Date of Patent: Oct. 17, 2023

(54) LUNG MICROBIOME ISOLATION AND CULTIVATION

(71) Applicant: University of South Florida, Tampa, FL (US)

(72) Inventors: Andreas Seyfang, Tampa, FL (US); Nirmal S. Sharma, Tampa, FL (US)

(73) Assignee: UNIVERSITY OF SOUTH FLORIDA, Tampa, FL (US)

( * ) Notice: Subject to any disclaimer, the term of this patent is extended or adjusted under 35 U.S.C. 154(b) by 0 days.

(21) Appl. No.: 16/893,579

(22) Filed: Jun. 5, 2020

Related U.S. Application Data

(60) Provisional application No. 62/857,939, filed on Jun. 6, 2019.

(51) Int. Cl.
*C12Q 1/689* (2018.01)
*A61K 35/747* (2015.01)

(52) U.S. Cl.
CPC ............ *C12Q 1/689* (2013.01); *A61K 35/747* (2013.01); *C12Q 2600/106* (2013.01); *C12Q 2600/16* (2013.01)

(58) Field of Classification Search
None
See application file for complete search history.

(56) References Cited

U.S. PATENT DOCUMENTS

| | | | |
|---|---|---|---|
| 7,341,841 B2 | 3/2008 | Metzger et al. | |
| 2011/0054247 A1* | 3/2011 | Sun | C12N 15/8509 600/34 |
| 2012/0207713 A1* | 8/2012 | MacSharry | A61P 5/00 424/93.4 |
| 2014/0199372 A1* | 7/2014 | Lewis | A61K 35/741 424/450 |
| 2017/0151268 A1* | 6/2017 | von Maltzahn | A61K 31/353 |
| 2018/0280574 A1* | 10/2018 | Gilbert | A61P 11/04 |

OTHER PUBLICATIONS

Baumeister et al. (Journal of clinical Microbiology Jul. 1998 p. 1984-1988) (Year: 1998).*
Leekha, et al 2011. General Principles of Antimicrobial Therapy. Mayo Clin Proc. 86(2): 156-167.
Zaccard et al. 2009. Efficacy of Bilateral Bronchoalveolar Lavage for Diagnosis of Ventilator-Associated Pneumonia. Journal of Clinical Microbiology, Sep. 2009, vol. 47, No. 9, p. 2918-2924.
Sproule-Willoughby et al. 2010. In vitro anaerobic biofilms of human colonic microbiota. Journal of Microbiological Methods, 83 (2010) 296-301.
Tryptic Soy Broth Brochure, 2014, Dalynn Biologicals, Calgary, Alberta, Canada.
Lactobacilli-MRS Broth Brochure, 2018, Anaerobe Systems, Morgan Hill, CA.
Chopped Meat Media Brochure, 2019, Hardy Diagnostics, Santa Maria, CA.

* cited by examiner

*Primary Examiner* — Katherine D Salmon
(74) *Attorney, Agent, or Firm* — QUARLES AND BRADY, LLP

(57) ABSTRACT

Disclosed herein is a method to isolate and cultivate the lung microbiome obtained from bronchoalveolar lavage. The disclosed method involves lung microbiome culturomics based on three different media for both aerobic and fastidious anaerobic bacteria. The disclosed method allows for amplification of the lung microbiome, which can be used, for example, for subsequent testing of antibiotic sensitivity, drug resistance, or for lung microbiome transplantation.

20 Claims, 5 Drawing Sheets

LUNG MICROBIOME ISOLATION AND CULTIVATION

CROSS-REFERENCE TO RELATED APPLICATIONS

This application claims benefit of U.S. Provisional Application No. 62/857,939, filed Jun. 6, 2019, which is hereby incorporated herein by reference in its entirety.

BACKGROUND

Recent studies suggest a role of the lung microbiome in the pathogenesis and progression of several chronic lung diseases such as asthma, chronic obstructive pulmonary disease (COPD), cystic fibrosis, idiopathic pulmonary fibrosis and transplant rejection. Asthma and COPD alone each independently affect more than 3 million US patients per year, cystic fibrosis affects about 200,000 US cases per year, and lung transplant remains the only curative option for several end stage lung diseases. Long term outcomes of lung transplantation and other chronic lung diseases are affected by the lung microbiome. Hence the favorable modulation of the dysbiosed or potentially harmful lung microbiome by replacing with a beneficial composition of lung microbiota obtained from bronchoalveolar lavage of healthy donors may impact the host immune response to reduce progression of lung diseases.

The lung microbiome is several orders of magnitude less abundant than for example the gut microbiome and the lung microbiome is highly variable in health and rejection of lung transplant. Likewise, the composition of the lung microbiome can be an important indicator and predictor of the outcome of a lung transplantation or the prognosis of several chronic lung diseases. Unfortunately, traditional hospital-based culture methods are unable to successfully isolate several microbes that are present in the lung lavage from patients.

SUMMARY

Disclosed herein is a method to isolate and cultivate the lung microbiome obtained from bronchoalveolar lavage. The disclosed method involves lung microbiome culturomics based on three different media for both aerobic and fastidious anaerobic bacteria. The disclosed method allows for amplification of the lung microbiome, which can be used, for example, for subsequent testing of antibiotic sensitivity, drug resistance, or for lung microbiome transplantation.

In particular, disclosed herein is a method for preparing an amplified lung microbiome from a subject that involves obtaining a bronchoalveolar lavage (BAL) sample from the subject; culturing a first portion of the BAL sample in a Tryptic Soy broth medium under conditions suitable to expand a first aerobic lung bacteria population; culturing a second portion of the BAL sample in a Lactobacilli-adapted MRS broth medium under conditions suitable to expand a second aerobic lung bacteria population; and culturing a third portion of the BAL sample in a modified Chopped Meat medium supplemented with DHNA (1,4-dihydroxy-2-naphthoic acid) under conditions suitable to expand first anaerobic lung bacteria population, wherein a mixture of the first aerobic lung bacteria population, second aerobic lung bacteria population, first anaerobic lung bacteria population, or any combination thereof, produces the amplified lung microbiome.

In some embodiments, the method further involves assaying the amplified lung microbiome for a panel of bacterial DNA. For example, the panel of bacterial DNA can be used to detect the bacterial classes Bacilli, Clostridia, Gammaproteobacteria, Fusobacteriia, Actinobacteria, Bacteroidia, Deltaproteobacteria, or any combination thereof.

In some embodiments, th testing of the subject will be used for prognosis of lung disease or assessment of the risk or predisposition for lung disease, even if the subject shows no symptoms of lung disease at the time. This method also includes subjects at a stage before they show symptoms of a lung disease.

In some embodiments, the method further involves testing the amplified lung microbiome for antibiotic sensitivity to identify a candidate antibiotic for treating the subject. Such antibiotics may include, but are not limited to, third-generation cephalosporins, quinolones, or penicillins. In some embodiments, the method further involves treating the subject with the candidate antibiotic.

In some embodiments, the method further involves testing the amplified lung microbiome for lung microbiome transplantation. Identification of beneficial or probiotic bacteria vs. harmful bacteria can be accomplished by characterization of the lung microbiome composition in healthy individuals compared to the changes occurring in lung microbiome composition in the dysbiosed or potentially harmful lung microbiome of patients with chronic lung disease. In some embodiments, the method further involves transplanting the amplified lung microbiome into the subject via bronchoscopy or an inhalation procedure using an aerosol of the amplified beneficial or probiotic lung microbiome.

In some embodiments, the method further involves cryopreserving the amplified lung microbiome at about −80° C. in a cryopreservation medium. Cryopreservation media are known in the art. For example, in some embodiments, the cryopreservation medium can be composed of 50% of the respective culturomics medium, 25% glycerol, and 25% deionized water. Other cryopreservation media can be a mixture of approximately 50% (e.g., 30-60%) of a culturomics medium with a range of glycerol concentrations (e.g., 15-30%) optimized for a specific microbiome composition or specific bacteria density (e.g., low density or high density) depending on the type or severity of early, acute or chronic lung disease.

In some embodiments, the subject of the disclosed methods has a chronic lung disease. In some embodiments, the subject of the disclosed methods has a transplanted lung. In some embodiments, the subject of the disclosed methods has tested negative for BAL microbiome by other methods.

The details of one or more embodiments of the invention are set forth in the accompanying drawings and the description below. Other features, objects, and advantages of the invention will be apparent from the description and drawings, and from the claims.

DETAILED DESCRIPTION

Figure 1A:
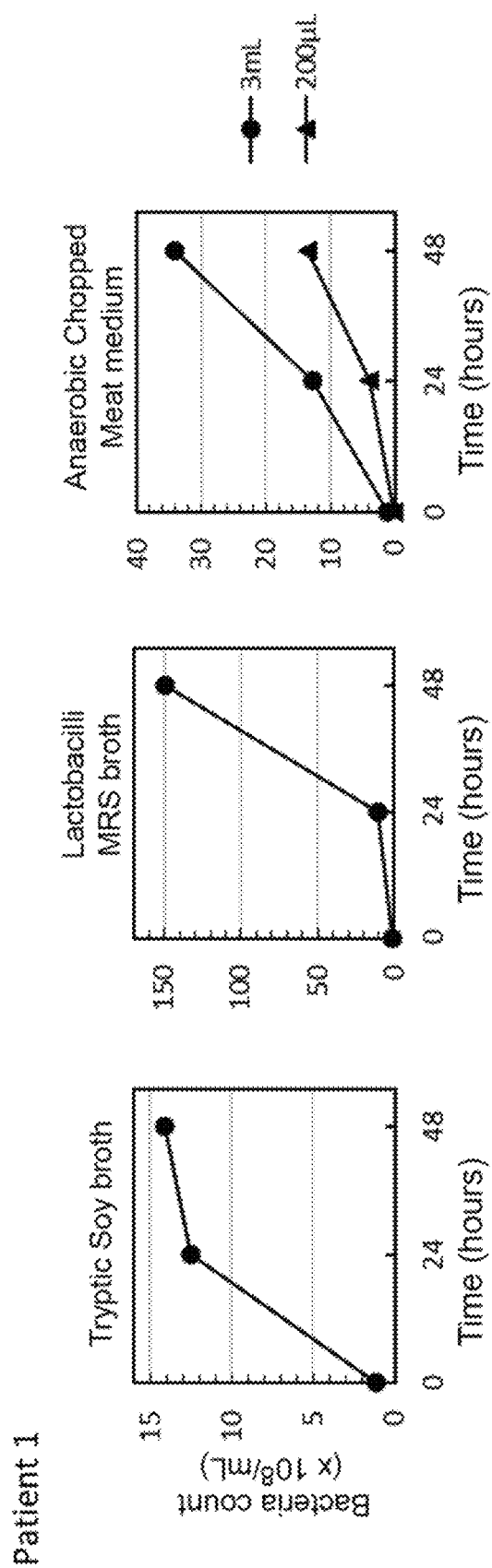
FIGS. 1A to 1D show lung microbiome cultivation using a combination of three different media for the growth of aerobic or fastidious anaerobic lung bacteria. Bronchoalveolar lavage was used to inoculate 2 mL of the respective medium and grown for 48 hours at 37° C. For 3 mL of lavage, bacteria were pelleted by centrifugation prior to inoculation, whereas for 200 µL or 20 µL inoculation volume the lavage was directly inoculated into the medium.
Figure 1B:
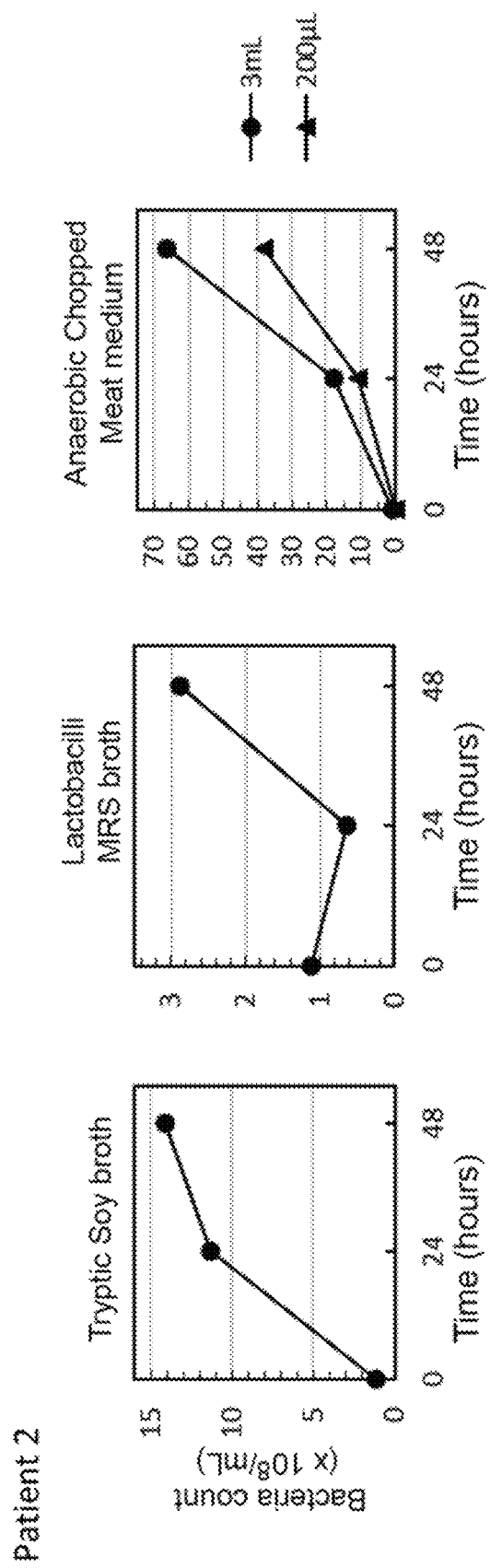
Figure 1C:
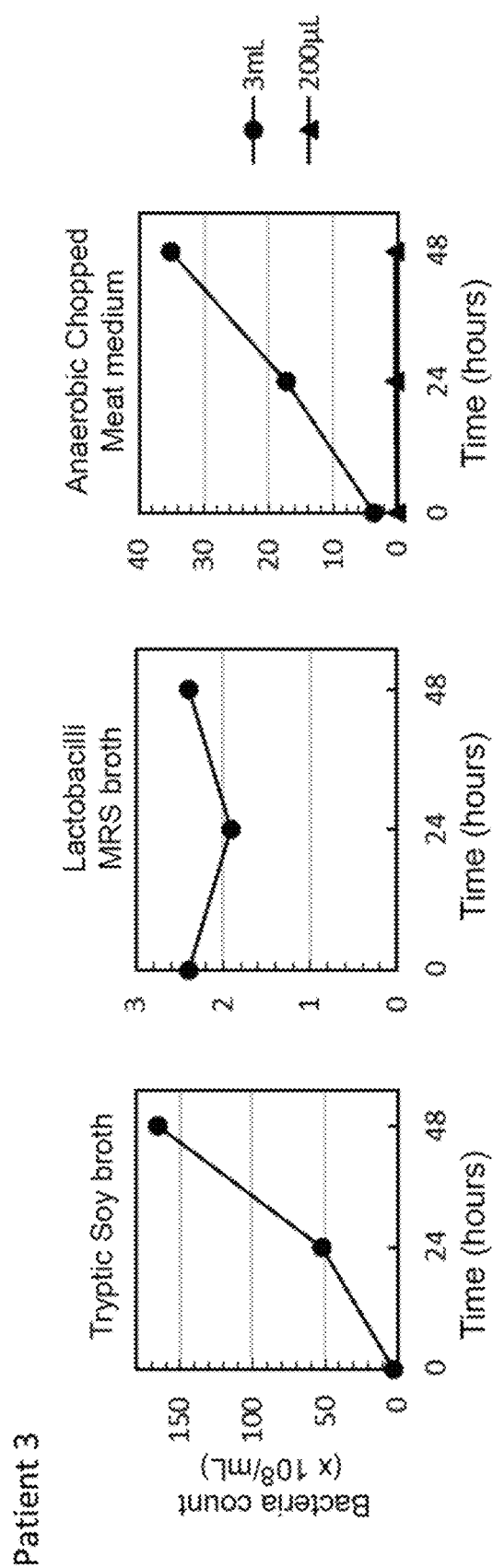
Figure 1D:
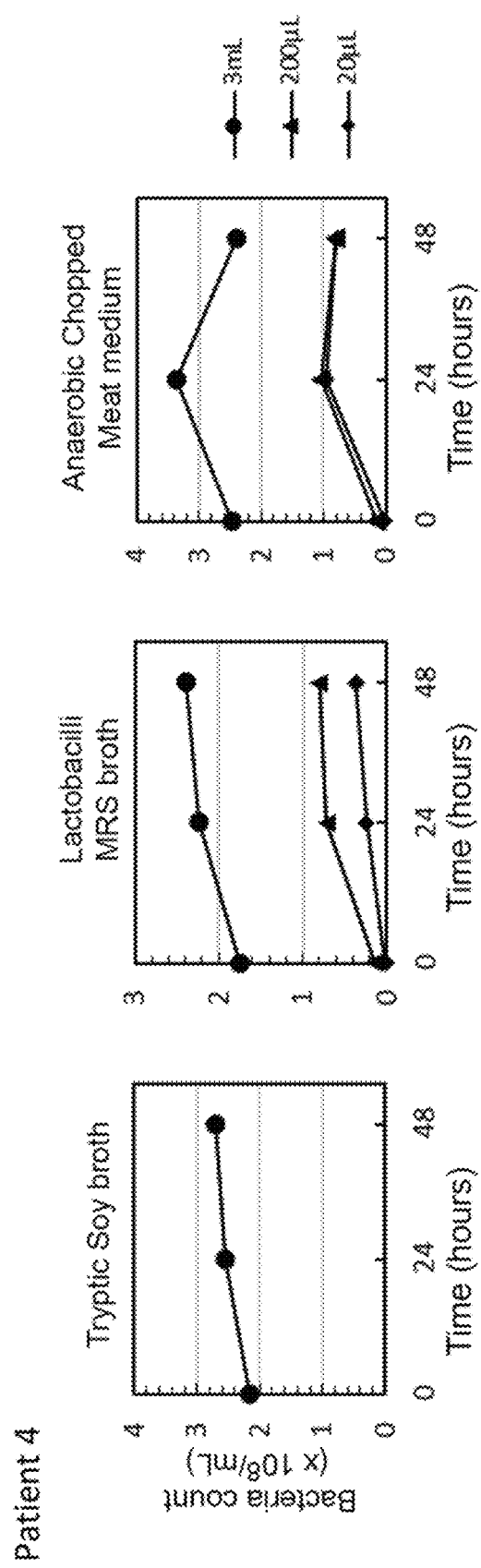

Before the present disclosure is described in greater detail, it is to be understood that this disclosure is not limited to particular embodiments described, and as such may vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of chemistry, biology, and the like, which are within the skill of the art.

The following examples are put forth so as to provide those of ordinary skill in the art with a complete disclosure and description of how to perform the methods and use the probes disclosed and claimed herein. Efforts have been made to ensure accuracy with respect to numbers (e.g., amounts, temperature, etc.) to the best ability, nevertheless some errors or deviations may be accounted for. Unless indicated otherwise, parts are parts by weight, temperature is in ° C., and pressure is at or near atmospheric. Standard temperature and pressure are defined as 20° C. and 1 atmosphere.

Before the embodiments of the present disclosure are described in detail, it is to be understood that, unless otherwise indicated, the present disclosure is not limited to particular materials, reagents, reaction materials, manufacturing processes, or the like, as such can vary. It is also to be understood that the terminology used herein is for purposes of describing particular embodiments only, and is not intended to be limiting. It is also possible in the present disclosure that steps can be executed in different sequence where this is logically possible.

It must be noted that, as used in the specification and the appended claims, the singular forms "a," "an," and "the" include plural referents unless the context clearly dictates otherwise.

The term "antibiotic" broadly refers to compounds capable of inhibiting or preventing a microbial infection, including a bacterial, fungal, or protozoan infection.

The term "bronchoalveolar lavage" or "BAL" refers to any medical procedure in which fluid (e.g., saline) is administered to a portion of a lung and re-collected for analysis. Upon re-collection, BAL fluid samples may contain biological components including but not limited to cells (e.g., microbiome). Typically, a bronchoscope is used for administration and collection of BAL fluid. BAL procedures and the samples obtained thereby are not limited by the region of the lung to which fluid is administered, the type of fluid administered, the volume of fluid administered, or any other aspects of the procedure (e.g., co-administration of anesthetic or antibiotic agents).

The term "cryoprotectant" refers to a substance that is added to a formulation in order to protect an active ingredient during freezing.

The term "lyoprotectant" refers to a substance that is added to a formulation in order to protect an active ingredient during the drying stage of a Lyophilization (also known as freeze-drying) process.

The term "microbiota" refers to the community of microorganisms that occur (sustainably or transiently) in and on an animal subject, typically a mammal such as a human, including eukaryotes, archaea, bacteria, and viruses (including bacterial viruses i.e., phages).

The term "microbiome" refers to the genetic content of the communities of microbes that live in and on the human body, both sustainably and transiently, including eukaryotes, archaea, bacteria, and viruses (including bacterial viruses (i.e., a phage)), wherein "genetic content" includes genomic DNA, RNA such as ribosomal RNA, the epigenome, plasmids, and all other types of genetic information.

The term "sample" is used in its broadest sense. For example, in some embodiments, it is meant to include a specimen (e.g., bronchoalveolar lavage sample) or culture (e.g., cell culture). In preferred embodiments, it is meant to include a biological sample.

The term "subject" refers to any individual who is the target of administration or treatment. The subject can be a vertebrate, for example, a mammal. Thus, the subject can be a human or veterinary patient. The term "patient" refers to a subject under the treatment of a clinician, e.g., physician.

The term "therapeutically effective" refers to the amount of the composition used is of sufficient quantity to ameliorate one or more causes or symptoms of a disease or disorder. Such amelioration only requires a reduction or alteration, not necessarily elimination.

Methods for Preparing an Amplified Lung Microbiome

Disclosed herein is a method to isolate and cultivate the lung microbiome obtained from bronchoalveolar lavage. The disclosed method involves lung microbiome culturomics based on three different media for both aerobic and fastidious anaerobic bacteria. In some embodiments, a Tryptic Soy broth medium and a Lactobacilli-adapted MRS broth medium can be used for growth of aerobic lung bacteria, and a modified Chopped Meat medium supplemented with DHNA (1,4-dihydroxy-2-naphthoic acid) was used for the growth of fastidious anaerobic lung bacteria for 24 to 48 hours.

The disclosed method allows for amplification of the lung microbiome, which can be used, for example, for subsequent testing of antibiotic sensitivity, drug resistance, or for lung microbiome transplantation. Remarkably, in a discovery cohort, all lung transplant patients tested bacteria-negative with standard hospital lavage laboratory tests, whereas in the disclosed method 3 mL or 200 µL of lavage fluid (out of a routine 120 mL fluid per routine lung lavage) was used to obtain very robust growth of lung bacteria cultures within 24 to 48 hours in the three different media to amplify the small amount of bacteria found in the patients' personalized lung microbiome. Bacteria growth profiles were very specific for each patient. Parallel negative controls for the lavage procedure were performed as well. Furthermore, a method is also disclosed to preserve live lung microbiome with a cryopreservation medium that allows one to successfully freeze and revive these lung microbiome cultures after prolonged storage. Hence this cryopreservation method of lung microbiome opens the potential not only for medical applications such as lung microbiome transplantation, but it also provides enough material to screen for optimal antibiotic treatment or potential bacteria drug resistance in a patient's lavage within 1-2 days, as well as for long-term follow-up clinical research on the personalized microbiome of a patient.

The disclosed method has several potential applications. Hence cultivation and amplification of individual lung microbiome from patients with chronic lung disease or lung transplantation could be used.

In some embodiments, the disclosed method is used to amplify the small amount of naturally occurring lung microbiome to sufficient quantities for subsequent lung microbiome transplantation and probiotic use of a beneficial composition of "good" lung microbiome via routine bronchoscopy or inhalation procedure.

In some embodiments, the disclosed method is used to amplify lung microbiome to analyze the patient's personal lung microbiome composition as an indicator and predictor for the prognosis and outcome of lung disease or success of lung transplantation as part of personalized medicine. This could also become a routine to screen patients with lung diseases for their risk to develop a worsening of their disease and hence earlier adequate intervention.

In some embodiments, the disclosed method is used as a more sensitive routine procedure to amplify and characterize the lung microbiome of patients where current routine lung lavage microbiome tests are negative. Hence the procedure of this invention could become a standard test for Quest Diagnostics and other clinical laboratories.

In some embodiments, the disclosed method is used to test the optimal antibiotic treatment in in vitro cultures for patients with a "bad" lung microbiome that is affecting their chronic lung disease.

In some embodiments, the disclosed method is used to screen in vitro as a laboratory routine for antibiotic resistance in patients with chronic lung disease or lung transplantation.

In some embodiments, the disclosed method is used to cryopreserve and store viable lung microbiome samples for long term storage and for later follow-up clinical analyses or biomedical research.

Therefore, disclosed herein is a method for preparing an amplified lung microbiome from a subject, that involves obtaining a bronchoalveolar lavage (BAL) sample from the subject; culturing a first portion of the BAL sample in a Tryptic Soy broth medium under conditions suitable to expand under conditions suitable to expand a first aerobic lung bacteria population; culturing a second portion of the BAL sample in a Lactobacilli-adapted MRS broth medium under conditions suitable to expand a second aerobic lung bacteria population; and culturing a third portion of the BAL sample in a modified Chopped Meat medium supplemented with DHNA (1,4-dihydroxy-2-naphthoic acid) under conditions suitable to expand first anaerobic lung bacteria population, wherein a mixture of the first aerobic lung bacteria population, second aerobic lung bacteria population, third anaerobic lung bacteria population, or any combination thereof, produces the amplified lung microbiome.

Tryptic Soy Broth Medium

Tryptic soy broth (TSB) is used in microbiology laboratories as a culture broth to grow aerobic bacteria. It is a complex, general purpose medium that is routinely used to grow certain pathogenic bacteria, which tend to have high nutritional requirements (i.e., they are fastidious). Its agar counterpart is tryptic soy agar (TSA). One of the components of Tryptic soy broth is a pancreatic digest of Casein (Tryptone). To prepare TSB, the following ingredients can be dissolved under gentle heat and then autoclaved for 15 minutes at 121° C. (250° F.): 17 grams of Tryptone, 3 grams of Soybean, 5 grams of sodium chloride, 2.5 grams of dipotassium phosphate ($K_2HPO_4$), 2.5 grams of glucose, and 1 liter of distilled water.

Lactobacilli-Adapted MRS Broth Medium

Lactobacilli MRS (deMan, Rogosa, and Sharpe) broth is an enriched selective medium for the cultivation of *Lactobacillus* from clinical, dairy, and food specimens. LMRS broth consists of Proteose Peptone no. 3, beef extract, yeast extract, and dextrose as the nutritive base. The medium is supplemented with Polysorbate 80 (Tween 80) and magnesium as a source of fatty acids and additional growth requirements. Sodium acetate and ammonium citrate may inhibit normal flora, such as gram-negative bacteria, oral flora, and fungi. Improved recovery of Lactobacilli occurs in the presence of these selective agents. The pH is adjusted to 6.3 to 6.7 to favor the growth of *Lactobacillus* spp. This medium is prepared, dispensed, and packaged under oxygen-free conditions to prevent the formation of oxidized products prior to use. Its counterpart is MRS agar.

MRS typically contains (w/v): 10.0 g/L Peptone, 10.0 g/L beef extract, 5.0 g/L yeast extract, 20.0 g/L glucose, 2.0 g/L potassium phosphate, 5.0 g/L sodium acetate, 0.1 g/L magnesium sulfate, 0.2 g/L manganese sulfate, 1.08 g/L polysorbate 80 (also known as Tween 80), 2.0 g/L ammonium citrate, and pH adjusted to 6.4 at 25° C. The yeast/meat extracts and peptone provide sources of carbon, nitrogen, and vitamins for general bacterial growth. The yeast extract also contains vitamins and amino acids specifically required by Lactobacilli. Polysorbate 80 is a surfactant which assists in nutrient uptake by Lactobacilli. Magnesium sulfate and manganese sulfate provide cations used in metabolism.

Modified Chopped Meat Medium

Chopped Meat Broths/Medium are pre-reduced anaerobically sterilized (PRAS) media used for the cultivation and maintenance of anaerobic bacteria. These media support the growth of most non-sporeforming and sporeforming obligate anaerobes associated with human and animal infections. The general nutritional components include pancreatic digest of casein and yeast extract, which provide vitamins and amino acids essential for growth. Hemin and vitamin K are also added since some anaerobes are directly stimulated by their presence. The chopped meat serves a multitude of purposes: the cooked meat provides substrate for proteolytic enzymes while the sulfahydryl groups of muscle protein have a reducing action and help maintain a favorable anaerobic environment. Cysteine is also a reducing agent and hence helps maintain anaerobiosis. The broth also contains the atmospheric indicator resazurin; in its reduced state the indicator is colorless, but in the presence of oxygen the indicator turns the broth pink. Various formulations are available containing different carbohydrates, including glucose, cellobiose, maltose, and starch. These media are generally prepared, dispensed, and packaged under oxygen-free conditions to prevent the formation of oxidized products prior to use.

In some embodiments, the Chopped Meat Medium is supplemented with DHNA (1,4-dihydroxy-2-naphthoic acid). In some cases, the Chopped Meat Medium is supplemented with DHNA at about 0.1 to 10 mg/L, including 0.1 to 1 mg/L, 1 to 10 mg/L, or 0.5 to 5 mg/L. In some cases, the Chopped Meat Medium is supplemented with DHNA at about 0.5, 0.6, 0.7, 0.8, 0.9, 1, 2, 3, 4, 5, 6, 7, 8, 9, or 10 mg/L Growth Conditions In various embodiments, microorganisms to be analyzed may be maintained in or subjected to one or more conditions suitable for growth. For example, the sample handling and detection systems described herein may include one or more sample vessels in which microorganism samples are placed for detection and analysis. In various embodiments, a sample vessel may comprise a disposable microfluidic flow-cell cassette having a plurality of separate cells (flowcells) or chambers into which microorganisms may be placed. The cassette and the flowcells may be configured, for example, as described in U.S. Pat. No. 7,341,841 (the entire contents of which are incorporated by reference herein), in a manner whereby it may be possible to regulate the media composition (including antibiotic presence and concentration), flow rate, temperature, pH, gas mixture, pressure, and any other environmental parameter that may be regulated in relation to microorganism growth. Likewise, the remainder of the system outside of the cassette may also be configured to provide for regulation and/or manipulation of any of a variety of environmental or external parameters.

In various embodiments and as used herein, a "condition" can be any parameter related to or having an influence on microorganism growth. For example, a "condition" can include parameters required for or beneficial to microorganism growth, and a "condition" can include parameters that may inhibit microorganism growth. Likewise, a "condition" can refer to a single parameter or variable that may influence microorganism growth, or a "condition" may collectively refer to a set of parameters or variables. A "condition" can include any traditional microbiological culture medium that may be known to a person of ordinary skill in the art, and a "condition" can further include any growth (or selective) medium comprising any combination of medium components, whether defined or undefined (complex). Examples of medium components and classes of components include carbon sources, nitrogen sources, amino acids, extracts, salts, metal ions, cofactors, vitamins, dissolved gasses, and the like. Similarly, a "condition" can include various components that might be added to a medium to influence the growth of a microorganism, such as selective and non-selective antimicrobial agents that may inhibit or arrest microorganism growth, modulating agents (i.e., agents that may alter microorganism growth but are not considered antimicrobial agents), or enrichment agents (e.g., substances that may be required for auxotrophic microorganisms, such as hemin, or substances that may be required by fastidious organisms) or other components that may encourage microorganism growth. A "condition" can also include other environmental parameters separate from the composition of a culture medium, such as light, pressure, temperature, concentration of oxygen or other gases (including anaerobic conditions) and the like. Similarly, a condition can include any of a variety of other parameters that might occur or be imposed, such as: a host organism defensive material or cell (e.g., human defensin proteins, complement, antibody, macrophage cell, etc.), a surface adherent material (i.e., surfaces intended to inhibit growth, kill cells, etc.), a physiological, metabolic, or gene expression modulating agent (e.g., host defense activation with co-cultured host cells), a physiological salt, metabolite, or metabolic waste materials (such as may be produced by living microorganisms or used to simulate late-stage culture growth conditions (i.e., stationary phase conditions), a reduction in nutrient media (simulating, for example, stationary phase conditions), or a bacteriophage infection (actual or simulated). Furthermore, a "condition" may be static (e.g. a fixed concentration or temperature) or dynamic (e.g. time-varying antimicrobial concentration to simulate pharmacokinetic behavior of intermittent infusions; or to simulate any endogenous or exogenous process affecting microbe response). These definitions of "condition" are intended to be illustrative, rather than exhaustive, and, as used herein, a "condition" can include any endogenous or exogenous parameter that may influence a microorganism.

In various embodiments, a system may include a temperature regulated incubation chamber in which the sample cassette may be maintained during microorganism detection and analysis. In various embodiments, a system may include ability to provide for temperature regulation of the cassette or sample chambers such as by using Peltier elements, resistive heating elements, or temperature regulation of circulating liquid medium for growth during or between evaluations. Temperature regulation may comprise maintaining a microorganism at a fixed temperature during an analysis period, or may comprise providing changing temperatures according to a predetermined temperature profile. A temperature regimen comprising changing temperature can include temperature changes at predetermined temperature change slopes or ramps. In various embodiments, temperature regulation may comprise simultaneously providing different temperatures or temperature profiles for individual chambers or flowcells in a cassette during an analysis period.

In some variations the system may be further configured to accelerate microorganism (and particularly bacterial) growth relative to standard clinical microbiological culturing conditions. Microorganism growth may be accelerated while evaluating growth by changing, for example, the temperature, composition, and/or oxygen content of the media. For example, increasing the temperature may provide an increased rate of microorganism growth and enable a determination of a rate of growth using the system and method disclosed herein in a shortened time frame relative to incubation at a temperature used in standard antibiotic susceptibility testing (AST) methods.

Evaluating the Amplified Lung Microbiome

In some embodiments, the disclosed method further involves assaying the amplified lung microbiome for a panel of bacterial DNA by 16S rRNA gene sequencing. In some embodiments, the panel of bacterial DNA detects bacterial classes including, but not limited to, Bacilli, Clostridia, Gammaproteobacteria, Fusobacteriia, Actinobacteria, Bacteroidia, Deltaproteobacteria, or any combination thereof. In some embodiments, the panel of bacterial DNA detects other taxonomic ranks or units including, but not limited to, bacterial phylum, order, family, genus, or species.

Isolation of bacterial genomic DNA from bacterial samples of patient BAL or culturomics cultures can be done by minicolumn chromatography specific for bacterial genomic DNA isolation using a cell disruption method of vortexing with silicon beads for 5 minutes in a bacterial lysis buffer that contains 0.5% beta-mercaptoethanol, for example the commercial Quick-DNA™ Fungal/Bacterial Microprep Kit (Zymo Research) including BashingBeads™ (Zymo Research) according to manufacturer's protocol.

Sequencing of the 16S rRNA gene of the bacterial DNA sample can be performed by polymerase chain reaction (PCR) amplification of the V4 region of the 16S rRNA gene, after which the PCR product of a 16S V4 amplicon library from individual samples can be used for microbial DNA sequencing by NextGen sequencing on the Illumina®MiSeq®platform. For metagenomic analysis of the sequencing data, QIIME pipeline (Quantitative Insights Into Microbial Ecology; www.qiime.org) and QIAGEN CLC Genomics Workbench platforms can be used.

Examples of bacterial taxa for the lung microbiome, or any combination thereof, at the level of phyla, class, and family can include, but are not limited to Phyla: Firmicutes, Fusobacteria, Bacteroidetes, Proteobacteria, Actinobacteria. Class: Clostridia, Fusobacteriia, Bacterioidia, Bacilli, Gammaproteobacteria, Deltaproteobacteria, Actinobacteria, Thermomicrobia, Deinococci. Family: Veillonellaceae, Prevotellaceae, Fusobacteriaceae, Streptococcaceae, Carnobacteriaceae, Lactobacillaceae, Leptotrichiaceae, Pasteurellaceae, Bdellovirbionaceae, Actinomycetaceae, Exiguobacteraceae, Lachnospiraceae, Mogibacteriaceae.

In some embodiments, the disclosed method further involves testing the amplified lung microbiome for antibiotic sensitivity to identify a candidate antibiotic for treating the subject. The disclosed method can therefore further involve treating the subject with the candidate antibiotic.

In some embodiments, the disclosed method further involves testing the amplified lung microbiome for lung microbiome transplantation.

The method of any one of claims 1 to 6, further comprising transplanting the amplified lung microbiome into the subject. Lung microbiome transplantation would include, but is not limited to, routine bronchoscopy or inhalation procedures.

Microorganism Detection

Once A lung microbiome HAS been amplified, individual microorganisms can be interrogated (e.g., optically, spectroscopically, or by sequencing of the 16S rRNA gene for metagenomic analysis) to characterize and/or identify the microorganisms in the sample. The interrogation or detection of an attribute of a microorganism can take place in a non-invasive manner that does not interfere with the integrity or viability of the microorganism, that is, attributes of a microorganism present in a sample can be detected and measured while the microorganism remains in the sample cassette. For more detailed taxonomic identification of microorganisms, metagenomic analysis of 16S rRNA gene sequencing can be used. This requires only a small amounts of bacterial sample (e.g., 10 to 100 microliter) for isolation of bacterial DNA that is further aided by the amplification of bacterial samples from patients using the culturomics methods of the present disclosure, The rapid amplification of patient samples overnight or within 24 hours of culturomics culture is considerably faster than traditional growth of bacterial colonies on agar plates that can take several days to up to a week. Along with automation of the procedure of DNA isolation and 16S rRNA gene sequencing, this may substantially increase the turnaround time from sample collection to high-resolution taxonomic identification of the bacterial composition of a patient sample. Furthermore, the reduced handling of potentially pathogenic samples may increase the safety of an identification or AST process relative to traditional clinical microbiological methods.

Any of a number of methods that may provide an ability to detect an attribute of a microorganism may be used in various embodiments. Examples of methods that may provide real-time or near real-time detection can include brightfield imaging, darkfield imaging, phase contrast imaging, fluorescence imaging, upconverting phosphor imaging, chemiluminescence imaging, evanescent imaging, near infra-red detection, confocal microscopy in conjunction with scattering, surface plasmon resonance ("SPR"), atomic force microscopy, and the like. Likewise, various combinations of detection methods may be used in parallel or in complementary fashion to detect one or more attributes of a microorganism in accordance with the present disclosure.

In various embodiments, spectroscopic methods can be used to detect one or more attributes of the microorganisms. These may include intrinsic properties, such as a property present within the microorganism in the absence of additional, exogenously provided agents, such as stains, dyes, binding agents, etc. In various embodiments, optical spectroscopic methods can be used to analyze one or more extrinsic attributes of a microorganism, for example, a property that can only be detected with the aid of additional agents. In various embodiments, a variety of types of spectroscopy can be used, including, for example, fluorescence spectroscopy, diffuse reflectance spectroscopy, infrared spectroscopy, terahertz spectroscopy, transmission and absorbance spectroscopy, Raman spectroscopy, including Surface Enhanced Raman Spectroscopy ("SERS"), Spatially Offset Raman spectroscopy ("SORS"), transmission Raman spectroscopy, and/or resonance Raman spectroscopy or any combination thereof.

Spectroscopic detection can be carried out by any technique known to those of skill in the art to be effective for detecting and/or identifying one or more intrinsic or extrinsic attributes of a microorganism. For example, front face fluorescence (where the excitation and emitted light enters and leaves the same optical surface, and if the sample is generally optically thick, the excitation light penetrates a very short distance into the sample and can be used for identification of microorganisms. Other forms of measurement, such as epifluorescence, reflectance, absorbance, and/or scatter measurements, can also be employed.

Typically, the light source, or excitation source, results in the excitation of the sample, followed by measurement of the emission of fluorescence of the sample at predetermined time points or continuously. Similarly, the reflected light from interaction of the excitation source with the sample may be measured to provide pertinent data for identification and/or characterization. The emission from the sample may be measured by any suitable means of spectral discrimination, such as by employing a spectrometer.

A sample illumination source, or excitation source, may be selected from any number of suitable light sources as known to those skilled in the art. Any portion of the electromagnetic spectrum that produces usable data can be used.

In various embodiments, detection methods may be used that rely on fluorescence signal (e.g., intrinsic fluorescence or fluorescence due to the presence of added indicator dyes) due to excitation by a UV, visible spectrum, or IR light source. The light sources can be continuum lamps such as a deuterium or xenon lamps for UV and/or a tungsten halogen lamp for visible/IR excitation. Since these light sources have a broad range of emission, the excitation band can be reduced using optical bandpass filters. Other methods for emission wavelength spectral width that may be utilized include an acousto-optic tunable filter, liquid crystal tunable filter, an array of optical interference filters, prism spectrograph, and the like. Alternatively, lasers are available in discrete wavelengths from the ultraviolet to the near infrared. Any of a variety of fluorescence signal-based multiplexing methods will be known to those skilled in the art and are within the scope of the present disclosure.

Alternatively, light emitting diodes can be used as narrowband excitation light sources. LED's are available from a peak wavelength of 240 nm to in excess of 700 nm with a spectral width of 20-40 nm. The same methods for the reduction of spectral width can be incorporated with the LED's to improve discrimination between excitation and emission spectra. In various embodiments, a plurality of narrowband light sources, such as LEDs or lasers, may be spatially and/or temporally multiplexed to provide a multi-wavelength excitation source.

The emission from the sample may be measured by any suitable means of spectral discrimination, most preferably employing a spectrometer. The spectrometer may be a scanning monochromator that detects specific emission wavelengths whereby the output from the monochromator is detected by a photomultiplier tube and/or the spectrometer may be configured as an imaging spectrograph whereby the output is detected by an imaging detector array such as a charge-coupled device ("CCD") camera or detector array. In one embodiment, a discriminator allows the observation of the fluorescence and/or scattering signal by a photodetection means (such as a photomultiplier tube, avalanche photodiode, CCD detector array, a complementary metal oxide semiconductor ("CMOS") area sensor array and/or electron multiplying charge coupled device ("EMCCD") detector array. Fluorescence signal strength at several different wavelengths are acquired and saved in a computer memory.

The detection of growth could also be accomplished using Raman spectroscopy. Raman spectroscopy is a non-contact technique where the sample is illuminated by laser radiation. The scattered light is either elastically or inelastically scattered by interaction with the molecules which comprise the microorganism. The elastically scattered light is referred to as Rayleigh scattering and the inelastically scattered light is Raman scattering. Raman spectroscopy has been shown to be a potentially viable method of microorganism identification and/or characterization by examination of the vibrational spectra of the microorganism.

The laser illumination and scattering collection optics are designed to focus the beam to a near-diffraction limited spot size. This size ensures adequate laser signal on the microbe since Raman scattering is very inefficient. The collection optics are designed to efficiently capture scattered light and couple it into an optical spectrometer for analysis. The Raman signal can be acquired at one or more locations and the subsequent signal averaged.

Once Raman spectra are obtained, they may be analyzed for location and strength of key peaks in the spectra. This data may be compared to a stored reference data set of known microorganisms so that determinations of, for example, Gram type, morphological information, and species identification, can be obtained. A reference data set from known microorganisms can be obtained in the system and methods described herein, or may be obtained from a third party.

To enhance Raman (SERS) and fluorescence signals, microorganisms could either be coated with gold and/or silver nanoparticles in a sample preparation step, and/or the inner optical surface could be pre-coated with metal colloids of particular size and shape. In various embodiments, the nanoparticles may be associated with microorganisms in a centrifugation step.

In various embodiments, spectra such as fluorescence spectra obtained using various methods described above may be used to perform identification of microorganisms. Reference spectra may be obtained for known microorganisms, thus allowing for correlation of measured sample data with characterization of the microorganisms of interest using various mathematical methods known to those skilled in the art. The measured test data from known microorganisms is stored in machine-readable memory, e.g., within the instrument itself or within an associated data processing device, such as a connected computer-based system. For example, the data from samples being tested by the instrument may be compared with the baseline or control measurements utilizing software routines known to or within the ability of persons skilled in the art to develop. More particularly, the data may be analyzed by a number of multivariate analysis methods, such as, for example, General Discriminant Analysis ("GDA"), Partial Least Squares Discriminant Analysis ("PLSDA"), Partial Least Squares regression, Principal Component Analysis ("PCA"), Parallel Factor Analysis ("PARAFAC"), Neural Network Analysis ("NNA") and/or Support Vector Machine ("SVM"). These methods may be used to classify unknown microorganisms of interest in the sample being tested into relevant groups (e.g., species) based on existing nomenclature, and/or into naturally occurring groups based on the organism's metabolism, pathogenicity and/or virulence in designing the system for evaluating, detecting and/or characterizing the organism as described herein.

In other embodiments, the microorganisms associated with a detection device can be interrogated using mass spectrometry techniques, such as MALDI-TOF mass spectrometry, desorption electrospray ionization ("DESI") mass spectrometry, GC mass spectrometry, LC mass spectrometry, electrospray ionization ("ESI") mass spectrometry and Selected Ion Flow Tube ("SIFT") spectrometry.

A variety of other detection methods and analytical tools have been used to detect and/or determine values associated with various attributes of a microorganism, including, for example, optical density, nephelometry, densiometry, flow cytometry, capillary electrophoresis, analytical chemistry and indicator-based methods of metabolite detection, protein output, molecular diagnostics, impedance, quartz crystal microbalance, bioluminescence, microcantilever sensors, and asynchronous magnetic bead rotation, among others. Of the various methods that have been described herein, some, such as various optics based methods, surface plasmon resonance, and atomic force microscopy, are compatible with non-destructive measurement or detection of individual, living microorganisms and can be used to evaluate microorganism growth and/or development of a multicellular clone. Some of these methods are furthermore capable of resolving and providing multiple measures or data points for a particular, individuated microorganism at any given point in time. Any method, as may be currently in practice or developed in the future, may be used to determine a value associated with an attribute of a microorganism for use in determining a growth rate, as disclosed herein.

Cryoperservation

An amplified lung microbiome may be preserved for banking. The organisms may be placed into a chemical milieu that protects from freezing (adding 'cryoprotectants'), drying ('lyoprotectants'), and/or osmotic shock ('osmoprotectants'), dispensing into multiple (optionally identical) containers to create a uniform bank, and then treating the culture for preservation. Containers are generally impermeable and have closures that assure isolation from the environment. Cryopreservation treatment is accomplished by freezing a liquid at ultra-low temperatures (e.g., at or below −80° C.). Dried preservation removes water from the culture by evaporation (in the case of spray drying or 'cool drying') or by sublimation (e.g., for freeze drying, spray freeze drying). Removal of water improves long-term microbial composition storage stability at temperatures elevated above cryogenic conditions. If the microbial composition comprises, for example, spore forming species and results in the production of spores, the final composition may be purified by additional means such as density gradient centrifugation and preserved. Microbial composition banking may be done by culturing and preserving the strains individually, or by mixing the strains together to create a combined bank. As an example of cryopreservation, a microbial composition culture may be harvested by centrifugation to pellet the cells from the culture medium, the supernatant decanted and replaced with fresh culture broth containing 15% glycerol. The culture can then be aliquoted into 1 mL cryotubes, sealed, and placed at −80° C. for long-term viability retention. This procedure achieves acceptable viability upon recovery from frozen storage.

Therefore, also provided are bacterial compositions for administration to subjects. In some embodiments, the bacterial compositions are combined with additional active and/or inactive materials in order to produce a final product, which may be in single dosage unit or in a multi-dose format.

In some embodiments, the composition comprises at least one carbohydrate. A "carbohydrate" refers to a sugar or polymer of sugars. The terms "saccharide," "polysaccharide," "carbohydrate," and "oligosaccharide" may be used interchangeably. Most carbohydrates are aldehydes or ketones with many hydroxyl groups, usually one on each carbon atom of the molecule. Carbohydrates generally have the molecular formula $C_nH_{2n}O_n$. A carbohydrate may be a monosaccharide, a disaccharide, trisaccharide, oligosaccharide, or polysaccharide. The most basic carbohydrate is a monosaccharide, such as glucose, sucrose, galactose, mannose, ribose, arabinose, xylose, and fructose. Disaccharides are two joined monosaccharides. Exemplary disaccharides include sucrose, maltose, cellobiose, and lactose. Typically, an oligosaccharide includes between three and six monosaccharide units (e.g., raffinose, stachyose), and polysaccharides include six or more monosaccharide units. Exemplary polysaccharides include starch, glycogen, and cellulose. Carbohydrates may contain modified saccharide units such as 2'-deoxyribose wherein a hydroxyl group is removed, 2'-fluororibose wherein a hydroxyl group is replaced with a fluorine, or N-acetylglucosamine, a nitrogen-containing form of glucose (e.g., 2'-fluororibose, deoxyribose, and hexose). Carbohydrates may exist in many different forms, for example, conformers, cyclic forms, acyclic forms, stereoisomers, tautomers, anomers, and isomers.

In some embodiments, the composition comprises at least one lipid. As used herein, a "lipid" includes fats, oils, triglycerides, cholesterol, phospholipids, fatty acids in any form including free fatty acids. Fats, oils and fatty acids can be saturated, unsaturated (cis or trans) or partially unsaturated (cis or trans). In some embodiments the lipid comprises at least one fatty acid selected from lauric acid (12:0), myristic acid (14:0), palmitic acid (16:0), palmitoleic acid (16:1), margaric acid (17:0), heptadecenoic acid (17:1), stearic acid (18:0), oleic acid (18:1), linoleic acid (18:2), linolenic acid (18:3), octadecatetraenoic acid (18:4), arachidic acid (20:0), eicosenoic acid (20:1), eicosadienoic acid (20:2), eicosatetraenoic acid (20:4), eicosapentaenoic acid (20:5) (EPA), docosanoic acid (22:0), docosenoic acid (22:1), docosapentaenoic acid (22:5), docosahexaenoic acid (22:6) (DHA), and tetracosanoic acid (24:0). In some embodiments the composition comprises at least one modified lipid, for example a lipid that has been modified by cooking.

In some embodiments, the composition comprises at least one supplemental mineral or mineral source. Examples of minerals include, without limitation: chloride, sodium, calcium, iron, chromium, copper, iodine, zinc, magnesium, manganese, molybdenum, phosphorus, potassium, and selenium. Suitable forms of any of the foregoing minerals include soluble mineral salts, slightly soluble mineral salts, insoluble mineral salts, chelated minerals, mineral complexes, non-reactive minerals such as carbonyl minerals, and reduced minerals, and combinations thereof.

In some embodiments, the composition comprises at least one supplemental vitamin. The at least one vitamin can be fat-soluble or water soluble vitamins. Suitable vitamins include but are not limited to vitamin C, vitamin A, vitamin E, vitamin B12, vitamin K, riboflavin, niacin, vitamin D, vitamin B6, folic acid, pyridoxine, thiamine, pantothenic acid, and biotin. Suitable forms of any of the foregoing are salts of the vitamin, derivatives of the vitamin, compounds having the same or similar activity of the vitamin, and metabolites of the vitamin.

In some embodiments, the composition comprises an excipient. Non-limiting examples of suitable excipients include a buffering agent, a preservative, a stabilizer, a binder, a compaction agent, a lubricant, a dispersion enhancer, a disintegration agent, a flavoring agent, a sweetener, and a coloring agent.

In some embodiments, the excipient is a buffering agent. Non-limiting examples of suitable buffering agents include sodium citrate, magnesium carbonate, magnesium bicarbonate, calcium carbonate, and calcium bicarbonate.

In some embodiments, the excipient comprises a preservative. Non-limiting examples of suitable preservatives include antioxidants, such as alpha-tocopherol and ascorbate, and antimicrobials, such as parabens, chlorobutanol, and phenol.

In some embodiments, the composition comprises a binder as an excipient. Non-limiting examples of suitable binders include starches, pregelatinized starches, gelatin, polyvinylpyrolidone, cellulose, methylcellulose, sodium carboxymethylcellulose, ethylcellulose, polyacrylamides, polyvinyloxoazolidone, polyvinylalcohols, C12-C18 fatty acid alcohol, polyethylene glycol, polyols, saccharides, oligosaccharides, and combinations thereof.

In some embodiments, the composition comprises a lubricant as an excipient. Non-limiting examples of suitable lubricants include magnesium stearate, calcium stearate, zinc stearate, hydrogenated vegetable oils, sterotex, polyoxyethylene monostearate, talc, polyethyleneglycol, sodium benzoate, sodium lauryl sulfate, magnesium lauryl sulfate, and light mineral oil.

In some embodiments, the composition comprises a dispersion enhancer as an excipient. Non-limiting examples of suitable dispersants include starch, alginic acid, polyvinylpyrrolidones, guar gum, kaolin, bentonite, purified wood cellulose, sodium starch glycolate, isoamorphous silicate, and microcrystalline cellulose as high HLB emulsifier surfactants.

In some embodiments, the composition comprises a disintegrant as an excipient. In some embodiments the disintegrant is a non-effervescent disintegrant. Non-limiting examples of suitable non-effervescent disintegrants include starches such as corn starch, potato starch, pregelatinized and modified starches thereof, sweeteners, clays, such as bentonite, micro-crystalline cellulose, alginates, sodium starch glycolate, gums such as agar, guar, locust bean, karaya, pectin, and tragacanth. In some embodiments the disintegrant is an effervescent disintegrant. Non-limiting examples of suitable effervescent disintegrants include sodium bicarbonate in combination with citric acid, and sodium bicarbonate in combination with tartaric acid.

Methods of Treatment

Also disclosed is a method for treating a subject with a lung condition, such as a disease, infection, or disorder, that involves preparing an amplified lung microbiome according to the disclosed methods, analyzing the amplified lung microbiome to identify a treatment for the subject, and then treating the subject. In some embodiments, the subject has a chronic lung disease. In some embodiments, the subject has a transplanted lung. In some embodiments, the subject has tested negative for BAL microbiome by other methods.

In some cases, the method involves assaying the amplified lung microbiome for a panel of bacterial DNA, e.g. from bacterial classes Bacilli, Clostridia, Gammaproteobacteria, Fusobacteriia, Actinobacteria, Bacteroidia, Deltaproteobacteria, or any combination thereof.

In some cases, the method involves testing the amplified lung microbiome for antibiotic sensitivity to identify a candidate antibiotic for treating the subject. In these embodiments, the method can further involve treating the subject with the candidate antibiotic.

Antibiotics can be classified in a number of ways, including their use for specific infections, their mechanism of action, their bioavailability, or their spectrum of target microbe (e.g., Gram-negative vs. Gram-positive bacteria, aerobic vs. anaerobic bacteria, etc.) and these may be used to kill specific bacteria in specific areas of the host ("niches") (Leekha, et al 2011. General Principles of Antimicrobial Therapy. Mayo Clin Proc. 86(2): 156-167). In certain embodiments, antibiotics can be used to selectively target bacteria of a specific niche. In some embodiments, antibiotics known to treat a particular infection that includes a cancer niche may be used to target cancer-associated microbes, including cancer-associated bacteria in that niche. In other embodiments, antibiotics are administered after the bacterial treatment. In some embodiments, antibiotics are administered after the bacterial treatment to remove the engraftment.

In some aspects, antibiotics can be selected based on their bactericidal or bacteriostatic properties. Bactericidal antibiotics include mechanisms of action that disrupt the cell wall (e.g., β-lactams), the cell membrane (e.g., daptomycin), or bacterial DNA (e.g., fluoroquinolones). Bacteriostatic agents inhibit bacterial replication and include sulfonamides, tetracyclines, and macrolides, and act by inhibiting protein synthesis. Furthermore, while some drugs can be bactericidal in certain organisms and bacteriostatic in others, knowing the target organism allows one skilled in the art to select an antibiotic with the appropriate properties. In certain treatment conditions, bacteriostatic antibiotics inhibit the activity of bactericidal antibiotics. Thus, in certain embodiments, bactericidal and bacteriostatic antibiotics are not combined.

Antibiotics include, but are not limited to aminoglycosides, ansamycins, carbacephems, carbapenems, cephalosporins, glycopeptides, lincosamides, lipopeptides, macrolides, monobactams, nitrofurans, oxazolidonones, penicillins, polypeptide antibiotics, quinolones, fluoroquinolone, sulfonamides, tetracyclines, and anti-mycobacterial compounds, and combinations thereof.

Aminoglycosides include, but are not limited to Amikacin, Gentamicin, Kanamycin, Neomycin, Netilmicin, Tobramycin, Paromomycin, and Spectinomycin. Aminoglycosides are effective, e.g., against Gram-negative bacteria, such as *Escherichia coli, Klebsiella, Pseudomonas aeruginosa*, and *Francisella tularensis*, and against certain aerobic bacteria but less effective against obligate/facultative anaerobes. Aminoglycosides are believed to bind to the bacterial 30S or 50S ribosomal subunit thereby inhibiting bacterial protein synthesis.

Ansamycins include, but are not limited to, Geldanamycin, Herbimycin, Rifamycin, and Streptovaricin. Geldanamycin and Herbimycin are believed to inhibit or alter the function of Heat Shock Protein 90.

Carbacephems include, but are not limited to, Loracarbef. Carbacephems are believed to inhibit bacterial cell wall synthesis.

Carbapenems include, but are not limited to, Ertapenem, Doripenem, Imipenem/Cilastatin, and Meropenem. Carbapenems are bactericidal for both Gram-positive and Gram-negative bacteria as broad-spectrum antibiotics. Carbapenems are believed to inhibit bacterial cell wall synthesis.

Cephalosporins include, but are not limited to, Cefadroxil, Cefazolin, Cefalotin, Cefalothin, Cefalexin, Cefaclor, Cefamandole, Cefoxitin, Cefprozil, Cefuroxime, Cefixime, Cefdinir, Cefditoren, Cefoperazone, Cefotaxime, Cefpodoxime, Ceftazidime, Ceftibuten, Ceftizoxime, Ceftriaxone, Cefepime, Ceftaroline fosamil, and Ceftobiprole. Selected Cephalosporins are effective, e.g., against Gram-negative bacteria and against Gram-positive bacteria, including *Pseudomonas*, certain Cephalosporins are effective against methicillin-resistant *Staphylococcus aureus* (MRSA).

Cephalosporins are believed to inhibit bacterial cell wall synthesis by disrupting synthesis of the peptidoglycan layer of bacterial cell walls.

Glycopeptides include, but are not limited to, Teicoplanin, Vancomycin, and Telavancin. Glycopeptides are effective, e.g., against aerobic and anaerobic Gram-positive bacteria including MRSA and *Clostridium difficile*. Glycopeptides are believed to inhibit bacterial cell wall synthesis by disrupting synthesis of the peptidoglycan layer of bacterial cell walls.

Lincosamides include, but are not limited to, Clindamycin and Lincomycin. Lincosamides are effective, e.g., against anaerobic bacteria, as well as *Staphylococcus*, and *Streptococcus*. Lincosamides are believed to bind to the bacterial 50S ribosomal subunit thereby inhibiting bacterial protein synthesis.

Lipopeptides include, but are not limited to, Daptomycin. Lipopeptides are effective, e.g., against Gram-positive bacteria. Lipopeptides are believed to bind to the bacterial membrane and cause rapid depolarization.

Macrolides include, but are not limited to, Azithromycin, Clarithromycin, Dirithromycin, Erythromycin, Roxithromycin, Troleandomycin, Telithromycin, and Spiramycin. Macrolides are effective, e.g., against *Streptococcus* and *Mycoplasma*. Macrolides are believed to bind to the bacterial or 50S ribosomal subunit, thereby inhibiting bacterial protein synthesis.

Monobactams include, but are not limited to, Aztreonam. Monobactams are effective, e.g., against Gram-negative bacteria. Monobactams are believed to inhibit bacterial cell wall synthesis by disrupting synthesis of the peptidoglycan layer of bacterial cell walls.

Nitrofurans include, but are not limited to, Furazolidone and Nitrofurantoin.

Oxazolidonones include, but are not limited to, Linezolid, Posizolid, Radezolid, and Torezolid. Oxazolidonones are believed to be protein synthesis inhibitors.

Penicillins include, but are not limited to, Amoxicillin, Ampicillin, Azlocillin, Carbenicillin, Cloxacillin, Dicloxacillin, Flucloxacillin, Mezlocillin, Methicillin, Nafcillin, Oxacillin, Penicillin G, Penicillin V, Piperacillin, Temocillin and Ticarcillin. Penicillins are effective, e.g., against Gram-positive bacteria, facultative anaerobes, e.g., *Streptococcus, Borrelia*, and *Treponema*. Penicillins are believed to inhibit bacterial cell wall synthesis by disrupting synthesis of the peptidoglycan layer of bacterial cell walls.

Penicillin combinations include, but are not limited to, Amoxicillin/clavulanate, Ampicillin/sulbactam, Piperacillin/tazobactam, and Ticarcillin/clavulanate.

Polypeptide antibiotics include, but are not limited to, Bacitracin, Colistin, and Polymyxin B and E. Polypeptide Antibiotics are effective, e.g., against Gram-negative bacteria. Certain polypeptide antibiotics are believed to inhibit isoprenyl pyrophosphate involved in synthesis of the peptidoglycan layer of bacterial cell walls, while others destabilize the bacterial outer membrane by displacing bacterial counter-ions.

Quinolones and Fluoroquinolone include, but are not limited to, Ciprofloxacin, Enoxacin, Gatifloxacin, Gemifloxacin, Levofloxacin, Lomefloxacin, Moxifloxacin, Nalidixic acid, Norfloxacin, Ofloxacin, Trovafloxacin, Grepafloxacin, Sparfloxacin, and Temafloxacin. Quinolones/Fluoroquinolone are effective, e.g., against *Streptococcus* and *Neisseria*. Quinolones/Fluoroquinolone are believed to inhibit the bacterial DNA gyrase or topoisomerase IV, thereby inhibiting DNA replication and transcription.

Sulfonamides include, but are not limited to, Mafenide, Sulfacetamide, Sulfadiazine, Silver sulfadiazine, Sulfadimethoxine, Sulfamethizole, Sulfamethoxazole, Sulfanilimide, Sulfasalazine, Sulfisoxazole, Trimethoprim-Sulfamethoxazole (Co-trimoxazole), and Sulfonamidochrysoidine. Sulfonamides are believed to inhibit folate synthesis by competitive inhibition of dihydropteroate synthetase, thereby inhibiting nucleic acid synthesis.

Tetracyclines include, but are not limited to, Demeclocycline, Doxycycline, Minocycline, Oxytetracycline, and Tetracycline. Tetracyclines are effective, e.g., against Gram-negative bacteria. Tetracyclines are believed to bind to the bacterial 30S ribosomal subunit thereby inhibiting bacterial protein synthesis.

Anti-mycobacterial compounds include, but are not limited to, Clofazimine, Dapsone, Capreomycin, Cycloserine, Ethambutol, Ethionamide, Isoniazid, Pyrazinamide, Rifampicin, Rifabutin, Rifapentine, and Streptomycin.

Suitable antibiotics also include arsphenamine, chloramphenicol, fosfomycin, fusidic acid, metronidazole, mupirocin, platensimycin, quinupristin/dalfopristin, tigecycline, tinidazole, trimethoprim amoxicillin/clavulanate, ampicillin/sulbactam, amphomycin ristocetin, azithromycin, bacitracin, buforin II, carbomycin, cecropin P1, clarithromycin, erythromycins, furazolidone, fusidic acid, Na fusidate, gramicidin, imipenem, indolicidin, josamycin, magainan II, metronidazole, nitroimidazoles, mikamycin, mutacin B-Ny266, mutacin B-JH1I 140, mutacin J-T8, nisin, nisin A, novobiocin, oleandomycin, ostreogrycin, piperacillin/tazobactam, pristinamycin, ramoplanin, ranalexin, reuterin, rifaximin, rosamicin, rosaramicin, spectinomycin, spiramycin, staphylomycin, streptogramin, streptogramin A, synergistin, taurolidine, teicoplanin, telithromycin, ticarcillin/clavulanic acid, triacetyloleandomycin, tylosin, tyrocidin, tyrothricin, vancomycin, vemamycin, and virginiamycin.

In some embodiments, the cancer therapy comprises administering a therapeutic bacteria and/or a therapeutic combination of bacteria to the subject so a healthy microbiome can be reconstituted in the subject. In some embodiments, the therapeutic bacteria is a non-cancer-associated bacteria. In some embodiments the therapeutic bacteria is a probiotic bacteria.

In some cases, the method involves testing the amplified lung microbiome for lung microbiome transplantation. In these embodiments, the method can further involve transplanting the amplified lung microbiome into the subject.

A number of embodiments of the invention have been described. Nevertheless, it will be understood that various modifications may be made without departing from the spirit and scope of the invention. Accordingly, other embodiments are within the scope of the following claims.

EXAMPLES

Example 1

Materials and Methods
Lung Microbiome Culturomics

For lung microbiome culturomics, bronchoalveolar lavage was used to inoculate three different media for both aerobic and fastidious anaerobic bacteria. A Tryptic Soy broth medium and a Lactobacilli-adapted MRS broth medium were used for growth of aerobic lung bacteria, and a modified Chopped Meat medium supplemented with DHNA (1 mg/L; 1,4-dihydroxy-2-naphthoic acid) was used for the growth of fastidious anaerobic lung bacteria for 24 to 48 hours at 37° C., in a rotary shaker for aerobic cultures or without shaking in an anaerobic incubation chamber, respectively. For anaerobic growth conditions, *Prevotella melaninogenica* reference strain VPI2381 (ATCC 25845) was used as control, which grew to a density of $28.8 \pm 4.1 \times 10^8$/mL ($OD_{600}$ of $3.6 \pm 0.5$) within 24 hours at anaerobic conditions but reached only $2.1 \times 10^8$/mL ($OD_{600}$ of 0.26) under aerobic conditions in otherwise identical medium. Furthermore, we also developed a method to preserve live lung microbiome with a cryopreservation medium that allows to successfully freeze and revive these lung microbiome cultures after prolonged storage at $-80°$ C.

Results

FIGS. 1A to 1D show lung microbiome cultivation using a combination of three different media for the growth of aerobic or fastidious anaerobic lung bacteria. Bronchoalveolar lavage was used to inoculate 2 mL of the respective medium and grown for 48 hours at 37° C. For 3 mL of lavage, bacteria were pelleted by centrifugation prior to inoculation, whereas for 200 μL or 20 μL inoculation volume the lavage was directly inoculated into the medium.

Table 1 shows growth of lung bacteria reference strains for *Pseudomonas aeruginosa* (aerobic) and *Prevotella melaninogenica* (anaerobic). For *Prevotella*, aerobic growth conditions inhibited growth as control for this anaerobic bacterium. All data are for 24 hour growth at 37° C. in Tryptic Soy broth medium under aerobic conditions for *P. aeruginosa* (PAO1 strain) or in modified Chopped Meat medium under anaerobic conditions for *Prevotella* (ATCC 25845 strain). Mean±standard deviation of 4-5 experiments.

TABLE 1

| | $OD_{600}$ | Bacteria Count ($\times 10^8$/mL) |
|---|---|---|
| *P. aeruginosa* (aerobic) | 4.86 ± 0.55 | 38.8 ± 4.4 |
| *Prevotella* (anaerobic) | 3.61 ± 0.51 | 28.8 ± 4.1 |
| *Prevotella* (aerobic control) | 0.26 | 2.1 |

Table 2 shows cryopreservation of lung microbiome cultures isolated from bronchoalveolar lavage and subsequent revival of bacterial cultures. Lung microbiome cultures after 48 hours were mixed with cryopreservation medium and frozen at $-80°$ C. for 10 days prior to revival of cultures and growth for 48 hours. Mean plus growth range for these heterogeneous cultures from different primary patient isolates. Doubling times of 8.5 to 9.7 hours of these heterogeneous cultures from primary patient isolates compare well with a doubling time of about 2 hours for laboratory adapted reference strains like *P. aeruginosa* PAO1.

Figure 2:
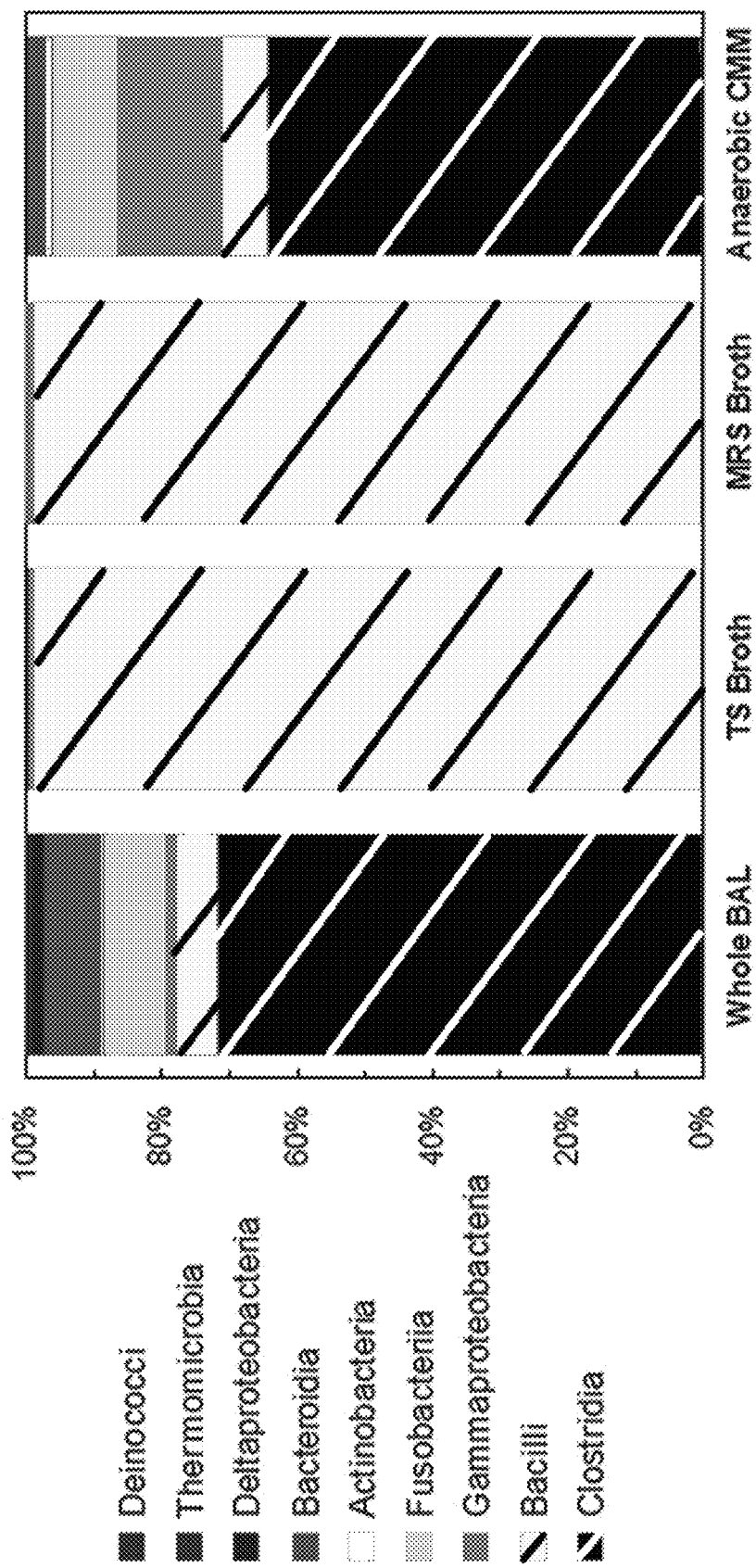
FIG. 2 shows lung microbiome composition in original bronchoalveolar lavage from patient as well as in samples from lung microbiome cultivation using a combination of three different media for the growth of aerobic or fastidious anaerobic lung bacteria. For lung microbiome culturomics, bronchoalveolar lavage (BAL) was used to inoculate 2 mL of the respective medium and grown at 37° C. Bacterial DNA was isolated from the BAL patient sample or after 24 hours of growth for the lung microbiome culturomics samples and metagenomic analysis of bacterial sample composition was performed by sequencing of the 16S rRNA gene. The nine different bacterial Classes represented in the patient BAL sample were also represented in the three lung culturomics media growth conditions. Individual media growth conditions allowed for enrichment of specific groups of bacteria.

FIG. 2 shows lung microbiome composition in original bronchoalveolar lavage from patient as well as in samples from lung microbiome cultivation using a combination of three different media for the growth of aerobic or fastidious anaerobic lung bacteria. For lung microbiome culturomics, bronchoalveolar lavage (BAL) was used to inoculate 2 mL of the respective medium and grown at 37° C. Bacterial DNA was isolated from the BAL patient sample or after 24 hours of growth for the lung microbiome culturomics samples and metagenomic analysis of bacterial sample composition was performed by sequencing of the 16S rRNA gene. The nine different bacterial Classes represented in the patient BAL sample were also represented in the three lung culturomics media growth conditions. Individual media growth conditions allowed for enrichment of specific groups of bacteria.

Table 3 shows lung microbiome metagenomic analysis in original bronchoalveolar lavage from patient as well as in samples from lung microbiome cultivation using a combination of three different media for the growth of aerobic or fastidious anaerobic lung bacteria. Bacterial DNA was isolated from the BAL patient sample or after 24 hours of growth for the lung microbiome culturomics samples and metagenomic analysis of bacterial sample composition was performed by sequencing of the 16S rRNA gene. Metagenomic analysis at the level of bacterial Phyla, Class, and Family is shown.

TABLE 2

Summary of Revival of Frozen Lavage Cultures

| | Cell count 0 hours | | Cell count 48 hours | | Amplification of frozen inoculum | | |
|---|---|---|---|---|---|---|---|
| | $\times 10^8$/2 mL | (range) | $\times 10^8$/2 mL | (range) | fold | (range) | doubling time |
| Tryptic Soy broth | 1.61 | (0.35-4.1) | 50.0 | (7.4-142.7) | 27.8 | (21.0-34.5) | 9.7 h |
| *Lactobacilli* MRS broth | 1.29 | (0.06-3.7) | 66.1 | (4.8-193.6) | 66.0 | (51.9-80.0) | 8.5 h |
| Anaerobic Chopped Meat medium | 1.13 | (0.06-1.7) | 37.4 | (2.9-59.5) | 36.2 | (28.8-48.0) | 9.5 h |

| | Whole BAL | TS Broth | MRS Broth | Anaerobic CMM |
|---|---|---|---|---|
| PHYLA | | | | |
| Firmicutes | 78 | 99 | 99 | 71 |
| Fusobacteria | 9 | 0 | 0 | 10 |
| Proteobacteria | 3.3 | 1 | 0.8 | 15 |
| Actinobacteria | 0.7 | 0 | 0.2 | 0.7 |
| Bacteroidetes | 8.5 | 0 | 0 | 3 |
| CLASS | | | | |
| Clostridia | 72 | 0 | 0 | 64 |
| Bacilli | 6 | 99 | 99 | 7 |
| Gammaproteobacteria | 1.7 | 0.5 | 0.8 | 15 |
| Fusobacteriia | 9 | 0 | 0 | 10 |
| Actinobacteria | 0.7 | 0 | 0.2 | 0.7 |
| Bacteroidia | 8.5 | 0 | 0 | 3 |
| Deltaproteobacteria | 1.6 | 0.5 | 0 | 0 |
| Thermomicrobia | 0.7 | 0 | 0 | 0 |
| Deinococci | 0.1 | 0 | 0 | 0 |
| FAMILY/CLASS (PHYLA) | | | | |
| Streptococcaceae/ Bacilli (Firmicutes) | 4 | 99 | 0 | 0 |
| Lactobacilluseae/Bacilli (Firmicutes) | 2 | 0 | 99 | 7 |
| Pasteurellaceae/ Gammaproteobacteria | 1.7 | 0.5 | 0.8 | 15 |
| Fusobacteriaceae/ Fusobacteriia | 7 | 0 | 0 | 9 |
| Bdellovirbionaceae/ Deltaproteobacteria | 1.6 | 0.5 | 0 | 3 |

-continued

| | Whole BAL | TS Broth | MRS Broth | Anaerobic CMM |
|---|---|---|---|---|
| Prevotellaceae/ Bacteroidia | 8.5 | 0 | 0 | 3 |
| Actinomycetaceae/ Actinobacteria | 0.7 | 0 | 0.2 | 0.7 |
| Carnobacteriaceae/ Bacilli (Firmicutes) | 2.4 | 0 | 0 | 0 |
| Veillonellaceae/ Clostridia (Firmicutes) | 66 | 0 | 0 | 64 |
| Lachnospiraceae/ Clostridia (Firmicutes) | 0.1 | 0 | 0 | 0 |
| Mogibacteriaceae/ Clostridia (Firmicutes) | 0.01 | 0 | 0 | 0 |
| Leptotrichiaceae/ Fusobacteriia | 2 | 0 | 0 | 0 |
| Exiguobacteraceae/ Bacilli (Firmicutes) | 0.5 | 0 | 0 | 0 |

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

What is claimed is:

1. A method for preparing an amplified lung microbiome from a subject, comprising
   (a) obtaining a bronchoalveolar lavage (BAL) sample from the subject;
   (b) culturing a first portion of the BAL sample in a liquid Tryptic Soy broth medium under conditions suitable to expand a first aerobic lung bacteria population;
   (c) culturing a second portion of the BAL sample in a liquid Lactobacilli-adapted MRS broth medium under conditions suitable to expand a second aerobic lung bacteria population; and
   (d) culturing a third portion of the BAL sample in a modified liquid Chopped Meat medium supplemented with DHNA (1,4-dihydroxy-2-naphthoic acid) under conditions suitable to expand a first anaerobic lung bacteria population,
   (e) mixing the first aerobic lung bacteria population, second aerobic lung bacteria population, and the first anaerobic lung bacteria population of steps (b)-(d) produces the amplified lung microbiome, wherein the amplified lung microbiome comprises bacteria from two or more of the following bacterial classes: gammaproteobacteria, fusobacteriia, actinobacteria, bacteroidia, and deltaproteobacteria.

2. The method of claim 1, further comprising assaying the amplified lung microbiome for a panel of bacterial DNA.

3. The method of claim 2, wherein the panel of bacterial DNA detects bacterial classes Gammaproteobacteria, Fusobacteriia, Actinobacteria, Bacteroidia, Deltaproteobacteria, or any combination thereof.

4. The method of claim 1, wherein the subject shows no symptoms of lung disease.

5. The method of claim 1, further comprising testing the amplified lung microbiome for antibiotic sensitivity to identify a candidate antibiotic for treating the subject.

6. The method of claim 5, further comprising treating the subject with the candidate antibiotic.

7. The method of claim 1, further comprising testing the amplified lung microbiome for lung microbiome transplantation.

8. The method of claim 1, further comprising transplanting the amplified lung microbiome into the subject.

9. The method of claim 1, further comprising cryopreserving the amplified lung microbiome at −80° C. in a cryopreservation medium.

10. The method of claim 1, wherein the subject has a chronic lung disease.

11. The method of claim 1, wherein the subject has a transplanted lung.

12. The method of claim 1, wherein the subject has tested bacteria-negative for BAL microbiome by other methods.

13. The method of claim 1, wherein the amplified lung microbiome comprises the following bacterial classes: Bacilli, Clostridia, Gammaproteobacteria, Fusobacteriia, Actinobacteria, Bacteroidia, and Deltaproteobacteria.

14. The method of claim 1, wherein the amplified lung microbiome comprises: (i) bacteria from the class Fusobacteriia, the class Bacteroidia, or both, from the third portion of the BAL sample cultured in the modified liquid Chopped Meat medium; (ii) bacteria from the class Deltaproteobacteria from the second portion of the BAL sample cultured in the liquid Tryptic Soy broth medium; and (iii) bacteria from the class Actinobacteria from: the second portion of the BAL sample cultured in the liquid Lactobacilli-adapted MRS broth, the third portion of the BAL sample cultured in the modified liquid Chopped Meat medium, or both.

15. A method of producing amplified, cryopreserved microbiome sample from bronchioalveolar lavage (BAL) fluid from a subject comprising:
   a. obtaining a bronchoalveolar lavage (BAL) sample from the subject;
   b. culturing a first portion of the BAL sample in a liquid Tryptic Soy broth medium under conditions suitable to expand a first aerobic lung bacteria population;
   c. culturing a second portion of the BAL sample in a liquid Lactobacilli-adapted MRS broth medium under conditions suitable to expand a second aerobic lung bacteria population; and
   d. culturing a third portion of the BAL sample in a modified liquid Chopped Meat medium supplemented with DHNA (1,4-dihydroxy-2-naphthoic acid) under conditions suitable to expand a first anaerobic lung bacteria population,
   e. combining a mixture of the first aerobic lung bacteria population, second aerobic lung bacteria population, and the first anaerobic lung bacteria population of steps (b)-(d) to produce the amplified lung microbiome,
   f. mixing the amplified lung microbiome with a cryopreservation medium, and
   g. freezing the amplified lung microbiome mixed with cryopreservation medium to produce an amplified, cryopreserved microbiome sample from bronchoalveolar lavage (BAL) fluid from a subject.

16. The method of claim 15, wherein the amplified, cryopreserved lung microbiome comprises bacteria from two or more of the following bacterial classes that are viable and capable of further growth: Gammaproteobacteria, Fusobacteriia, Actinobacteria, Bacteroidia, and Deltaproteobacteria.

17. The method of claim 16, wherein the amplified, cryopreserved lung microbiome comprises bacteria from the following bacterial classes that are viable and capable of further growth: Bacilli, Clostridia, Gammaproteobacteria, Fusobacteriia, Actinobacteria, Bacteroidia, and Deltaproteobacteria.

18. A method of amplifying a microbiome from bronchioalveolar lavage (BAL) fluid from a subject which has tested bacteria-negative by standard hospital lavage laboratory tests, the method comprising
   a. obtaining a bronchoalveolar lavage (BAL) sample from a subject who has previously tested bacteria-negative by standard hospital lavage laboratory tests;
   b. culturing a first portion of the BAL sample in a liquid Tryptic Soy broth medium under conditions suitable to expand a first aerobic lung bacteria population;
   c. culturing a second portion of the BAL sample in a liquid Lactobacilli-adapted MRS broth medium under conditions suitable to expand a second aerobic lung bacteria population; and
   d. culturing a third portion of the BAL sample in a modified Chopped Meat medium supplemented with DHNA (1,4-dihydroxy-2-naphthoic acid) under conditions suitable to expand a first anaerobic lung bacteria population,
   e. mixing the first aerobic lung bacteria population, second aerobic lung bacteria population, and the first anaerobic lung bacteria population produces the amplified lung microbiome from the subject.

19. The method of claim 18, wherein the amplified lung microbiome comprises bacteria from two or more of the following bacterial classes: Gammaproteobacteria, Fusobacteriia, Actinobacteria, Bacteroidia, and Deltaproteobacteria.

20. The method of claim 19, wherein the amplified lung microbiome comprises bacteria from the following bacterial classes: Bacilli, Clostridia, Gammaproteobacteria, Fusobacteriia, Actinobacteria, Bacteroidia, and Deltaproteobacteria.

* * * * *